United States Patent [19]

Politte et al.

[11] 4,285,708
[45] Aug. 25, 1981

[54] DE-ETHANIZING MEANS

[75] Inventors: Leo L. Politte; Stone P. Washer, both of Bartlesville, Okla.

[73] Assignee: Phillips Petroleum Co., Bartlesville, Okla.

[21] Appl. No.: 65,500

[22] Filed: Aug. 10, 1979

[51] Int. Cl.$^3$ .............................................. F25J 3/02
[52] U.S. Cl. ........................................ 62/28; 62/23; 62/42
[58] Field of Search ................................... 62/23–28, 62/42

[56] References Cited

U.S. PATENT DOCUMENTS

| | | | |
|---|---|---|---|
| 2,557,171 | 6/1951 | Bodle et al. | 62/23 |
| 2,581,088 | 1/1952 | Etherington et al. | 62/2 |
| 2,666,019 | 1/1954 | Winn et al. | 62/23 |
| 3,094,401 | 6/1963 | Lidell | 55/206 |
| 3,150,199 | 9/1964 | Greco et al. | 260/677 |
| 3,359,743 | 12/1967 | Di Napoli | 62/28 |
| 3,420,068 | 1/1969 | Petit | 62/27 |
| 3,516,261 | 6/1970 | Hoffman | 62/24 |
| 3,595,782 | 7/1971 | Bucklin et al. | 62/27 |
| 3,625,016 | 12/1971 | Hoffman | 62/26 |
| 3,656,312 | 4/1972 | Streich | 62/28 |
| 4,185,978 | 1/1980 | McGalliard et al. | 62/28 |

*Primary Examiner*—Norman Yudkoff

[57] ABSTRACT

Ethane is removed from a feedstream comprising methane, ethane and higher components by dividing the feedstream and passing one stream directly to the de-ethanizer with the other stream being passed to a stabilizer in order to remove the heavier components of the natural gas stream. The overhead vapor from the stabilizer is then passed to the de-ethanizer. The overhead vapor stream passed to the de-ethanizer from the stabilizer can also be cooled in order to reduce the refrigeration load of the de-ethanizer.

9 Claims, 1 Drawing Figure

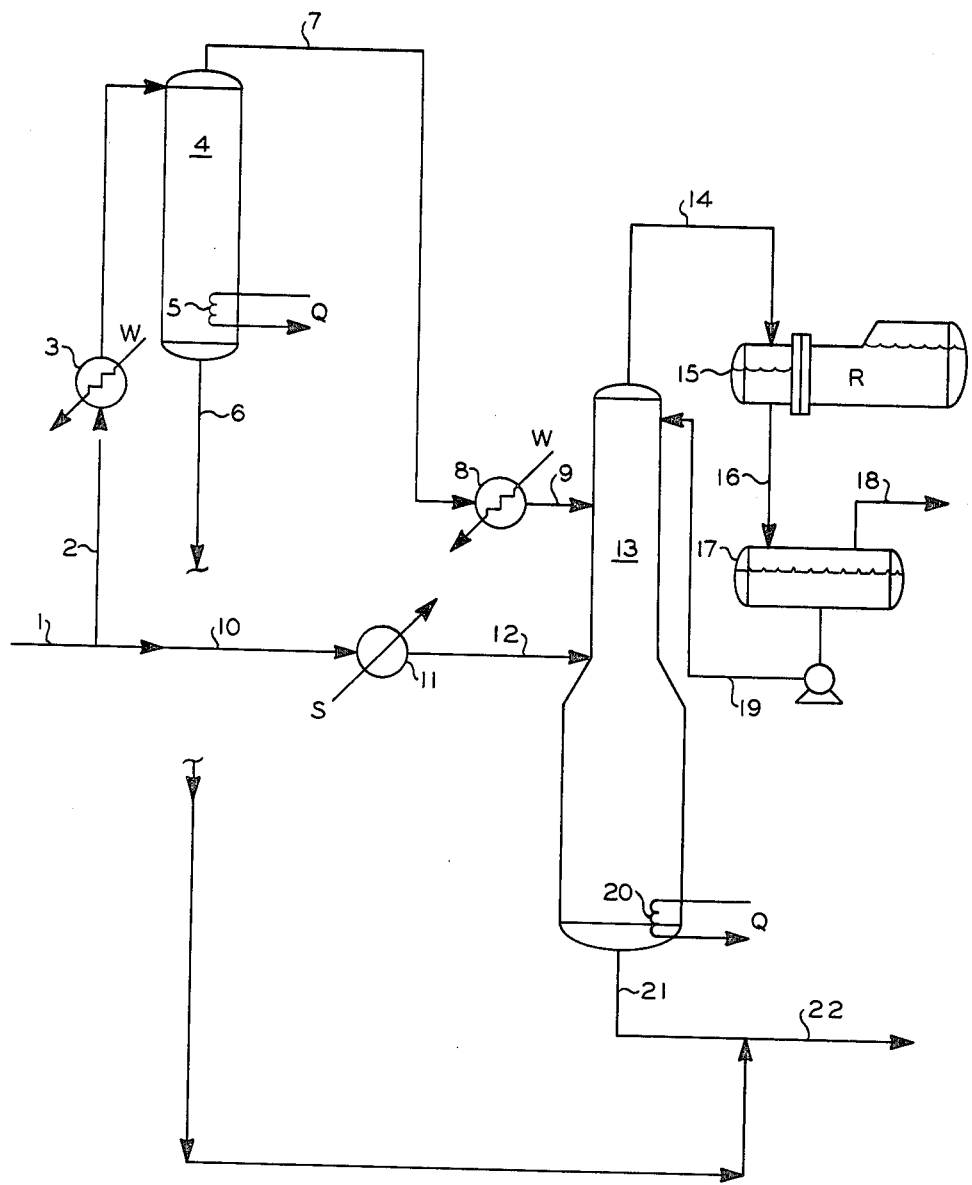

DE-ETHANIZING MEANS

BACKGROUND OF THE INVENTION

The present invention relates to the separation of a mixture of hydrocarbons. In another aspect, this invention relates to the separation of methane and ethane from higher hydrocarbon components such as propane, butane, pentane, and other heavier components present in natural gas. In another aspect, this invention relates to an apparatus useful for de-ethanizing a feedstream wherein said apparatus comprises a de-ethanizer column and a stabilizer. In another aspect, this invention relates to a process for de-ethanizing natural gas liquids wherein the feedstream is put into two streams with one stream being passed directly to the de-ethanizer and the other stream being passed to a stabilizer. In still another aspect, this invention relates to a process for de-ethanizing natural gas liquids wherein a portion of the feedstream is sent to a stabilizer and the overhead vapor obtained from the stabilizer column is passed to the de-ethanizer. In still another aspect, this invention relates to a process of de-ethanizing a natural gas liquids stream wherein a portion of the feedstream is passed to a stabilizer and the feed to the stabilizer and the overhead vapor to the de-ethanizer is cooled by heat exchange means. Another aspect of this invention relates to a process for de-ethanizing natural gas liquids wherein a portion of the feedstream is passed to a stabilizer and the overhead from the stabilizer is passed to the de-ethanizer with the location of introduction of said overhead vapor stream to the de-ethanizer being above the point of introduction of the direct feedstream.

Most natural gas liquids produced are composed of a wide range of hydrocarbons, e.g., "noncondensable" gases such as methane and ethane and "condensable" components such as propane, the butanes and heavier components. It is generally desirable to remove the heavier, condensable components from the methane/ethane components. The separation of the heavier components from the methane/ethane components eliminates problems in the long distance gas transmission of the methane/ethane gases and also allows one to market the heavier components as motor fuel. The cost of building such extraction de-ethanizing facilities can be an exorbitant amount, therefore, it would be understandably desirable to develop a plant which would satisfactorily extract the heavier components from the methane/ethane in an economical manner, e.g., a plant of less expense, smaller size and greater efficiency.

Several frequent problems encountered in a de-ethanizing process are the limitation on the capacity of the de-ethanizer due to the liquid loading in the bottom section of the tower and the greater energy requirements of the de-ethanizer in cooling the overhead vapor to form reflux. A de-ethanizing process which increases the capacity of the de-ethanizer and reduces the refrigeration load on the de-ethanizer as compared to existing processes would, therefore, be desirable in view of the exorbitant cost of building a de-ethanizing plant and the high cost of energy. Especially desirable would be a rather inexpensive and simple change which can be made in existing plants to eliminate such problems as opposed to having to build an entirely new plant in order to increase the capacity and decrease the refrigeration load on the de-ethanizer.

Accordingly, it is an object of this invention to provide an improved de-ethanizing system wherein the limited capacity of the de-ethanizer is increased.

Another object of the present invention is to reduce the refrigeration load on a de-ethanizer.

Still another aspect of this invention is to provide an apparatus set-up which increases the limited capacity of the de-ethanizer and reduces the refrigeration load on the de-ethanizer.

Another object of this invention is to provide an improved separation of relatively low boiling liquids or absorbed gases from a mixture containing these materials and relatively high boiling liquids by a combination of a de-ethanizer and a stabilizer.

Other objects, aspects, and the several advantages of this invention will be apparent to those skilled in the art upon a study of this disclosure, the appended claims, and the drawing.

SUMMARY OF THE INVENTION

In accordance with this invention, the limited capacity of a de-ethanizer is increased by using a stabilizer column. The process of the present invention comprises splitting the incoming feed, e.g., natural gas liquids, into two streams. One stream is passed to the stabilizer with the second stream being passed directly to the de-ethanizer. The stream passed to the stabilizer is generally introduced in the upper portion of the stabilizer with the second stream being passed to the mid-section of the de-ethanizer. The heavies from the stabilizer are removed as product, while the overhead vapor is passed to the de-ethanizer. The overhead vapor is introduced into the de-ethanizer at a point above the location of introduction of the feedstream passed directly to the de-ethanizer, e.g., the overhead vapor from the stabilizer is passed to the upper portion of the de-ethanizer while the direct feedstream is passed to the mid-section of the de-ethanizer. The de-ethanizer gasoline liquid is removed from the de-ethanizer as bottoms to join the heavies from the stabilizer as a product.

The overhead vapor from the de-ethanizer is condensed and recycled to the same column to act as reflux. This requires a great deal of refrigeration, therefore, in order to reduce the refrigeration load on the de-ethanizer, it is preferred that the feed to the stabilizer is precooled and that the overhead vapor passed to the de-ethanizer also be cooled. The two cooling steps conserve energy in the entire process as well as reduce the refrigeration load on the de-ethanizer.

BRIEF DESCRIPTION OF THE DRAWING

The drawing illustrates schematically a preferred set-up of the present invention which comprises a de-ethanizer and a stabilizer associated therewith.

DETAILED DESCRIPTION OF THE INVENTION

The present invention provides an improved process and apparatus for the separation of relatively low boiling liquids or absorbed gases from a mixture containing these materials and relatively high boiling liquids. The apparatus employed comprises, in combination, a de-ethanizer and a stabilizer. The mixtures fractionated in the de-ethanizer can be natural gas liquids, feed obtained from hydrocarbon refineries, or, more specifically, a hydrocarbon mixture comprising methane, ethane and higher components. The present invention has specific application to the separation of methane and ethane from higher hydrocarbon components such as propane, butane, pentane, and heavier components obtained from a natural gas source.

The apparatus set-up of the present invention comprises a fractionating means, e.g., a de-ethanizer, with a first conduit means for passing a feedstream, such as natural gas liquids, to the de-ethanizer. The fractionator or de-ethanizer can be of any particular size or shape as are well known in the art. Similarly, there is no criticality to the type of conduit means used in the present invention as any well known conduit would be appropriate for practicing the invention.

The apparatus setup also comprises a stabilizing means for removing the heavy components of the natural gas liquids stream passed to the stabilizer to thereby increase the capacity of the de-ethanizer. A second conduit means is used for passing the natural gas liquids from the first conduit means to the stabilizer. It is preferred that the second conduit means is connected to an introduction means in the upper portion of the stabilizer as it is preferred to introduce the feed into the upper portion of the stabilizer.

A third conduit means is used for passing the overhead vapor from the stabilizer to the de-ethanizing means. It is preferred that the overhead vapor is introduced at a location above the location at which the direct natural gas feedstream is introduced to the de-ethanizer. Since it is preferred that the direct natural gas liquids feedstream introduced to the de-ethanizer through the first conduit means be introduced at the mid-section of the de-ethanizer, it is generally preferred that the overhead vapor passed to the de-ethanizer be introduced in the upper portion of the de-ethanizer. The third conduit means, therefore, is connected to an introduction means located in the upper section of the de-ethanizing means and the first conduit means is connected to an introduction means in the mid-section of the de-ethanizer.

The overhead vapor from the de-ethanizer is then condensed and partially recycled to the column to act as reflux as is well known in the prior art. In another embodiment of this invention, however, the refrigeration load on the de-ethanizer is greatly reduced by precooling the feed to the stabilizer and the overhead vapor from the stabilizer. These precooling steps also save energy on the overall system.

In a preferred embodiment, therefore, the third conduit means passes through a heat exchange means for cooling the overhead vapor being passed from the stabilizer to the de-ethanizer and the second conduit means also passes through a heat exchange means for cooling the natural gas being fed from the first conduit means to the stabilizer.

The process of the present invention, therefore, comprises splitting the incoming feed of natural gas liquids into two streams. The first stream is passed to the stabilizer, preferably the upper section, with the second stream being passed to the de-ethanizer. The overhead vapor from the stabilizer is then passed to the de-ethanizer and introduced therein at a point above the point of introduction of the direct feedstream. A part of the overhead vapor from the de-ethanizer is condensed and recycled to the column with the heavies from the stabilizer and the bottoms from the column being removed as de-ethanized gasoline product.

In the preferred embodiment, the feedstream to the stabilizer and the overhead vapor passed to the de-ethanizer are cooled in order to save energy. The particular type of heat exchange employed is not of particular importance. As well, any well known heat exchange medium can also be employed, e.g., water, propane, or the like.

A distinct advantage of this process is the increased capacity of liquid loading in the de-ethanizer as a result of the stabilizer associated with the de-ethanizer. In effect, part of the heavy ends of the natural gasoline liquids is processed in the stabilizer to reduce the load on the de-ethanizer. Only the light ends separated in the stabilizer are further processed in the de-ethanizer.

Another advantage is the reduction of the refrigeration load on the de-ethanizer when the feed to the stabilizer and the overhead vapor to the de-ethanizer are cooled by heat exchange. Inexpensive water cooling can be employed in the two heat exchange steps thereby saving economically with regard to high cost refrigeration as employed in the de-ethanizer condenser. The two heat exchange steps conserve energy with regard to the entire process and can result in a savings of refrigeration of 1 million BTU/hr or more.

The use of the stabilizer in conjunction with the de-ethanizer, therefore, provides an increase in the capacity of a de-ethanizer without having to build a larger de-ethanizer and allows one to make a simple change in an already existing plant to increase the capacity thereof. Furthermore, the cooling aspects of the present invention allow one to conserve energy, which is extremely important due to present day energy consciousness and the high cost of energy.

A better understanding of the invention will be obtained upon reference to the drawing. Referring to the drawing, a feedstream 1, such as natural gasoline liquid, is split into two streams, a first stream 2 and a second stream 10. The first stream 2 is fed to a stabilizer column 4. Said stream can be precooled by a heat exchange means such as 3. Heating coils 5 are used to supply heat to the stabilizer. The heavies in stream 2 are removed as bottoms product 6 with the overhead vapor 7 being passed to de-ethanizer 13. Stream 7 can also be cooled by heat exchange means 8. The cooling steps, 3 and 8, result in an energy savings for the entire system by reducing the refrigeration load on the de-ethanizer.

The second stream 10 is fed directly to the de-ethanizer and introduced at 12. The stream can be preheated by a conventional heat exchange means 11. It is preferred that the second stream is introduced at the mid-section of the de-ethanizer with the location of introduction of the overhead vapor stream 7 being at some point above the mid-section 9, i.e., in the upper section of the de-ethanizer.

Heating coils 20 are used to reboil the de-ethanizer with heavy bottoms 21 being combined with bottoms product 6 to form a de-ethanized gasoline stream 22. The overhead vapor from the de-ethanizer 14 is cooled in a conventional heat exchange means 15 in order to condense said vapor which is passed via 16 to accumulating tank 17. Conventional refrigerants can be used in 15, with propane being preferred. Noncondensed vapor is vented from accumulator 17 via 18 with a part of the condensed vapor being pumped via 19 to the top of the de-ethanizer to act as reflux.

The following table relates to the process illustrated in the drawing and gives one example of some typical operating conditions which can be employed in the practice of the present invention. The following operating conditions are set forth only as illustrative, however, and are not meant to be restrictive.

| | | | |
|---|---|---|---|
| 1. Feed, natural gasoline liquid | 85000 B/D | 100° F. | 400 PSIA |
| 2. Portion of the feed | 25000 B/D | 100° F. | 460 PSIA |
| 3. Water precooler | 3-4MM BTU/Hr | | |
| 4. Stabilizer, upper section | | | 434 PSIA |
| bottom section | | | 438 PSIA |
| 5. Heating coils | 18.7MM BTU/Hr | | |
| 6. Heavier components of natural gasoline liquid | 18000 B/D | 250° F. | 438 PSIA |
| 7. Ethane + heavies | 7000 B/D | 139° F. | 434 PSIA |
| 8. Water precooler | 4.7MM BTU/Hr | | |
| 9. Precooled ethane and heavies to the DeC$_2$ | 7000 B/D | 90° F. | 433 PSIA |
| 10. Another portion of the feed | 60000 B/D | 100° F. | 460 PSIA |
| 11. Preheater for the other portion of the feed | 10MM BTU/Hr | | |
| 12. Preheated portion of the feed | 60000 B/D | 165° F. | 434 PSIA |
| 13. De-ethanizer, upper section | | 110° F. | 432 PSIA |
| lower section | | 241° F. | 439 PSIA |
| 14. Overhead of DeC$_2$ (condensed) | 35000 B/D | 98° F. | 432 PSIA |
| 15. Condenser | 19.97MM BTU/Hr | | |
| 16. Partially condensed overhead two phase | 20000 vapor B/D | 76° F. | 405 PSIA |
| | 15000 liquid B/D | | |
| 17. Accumulator | | | |
| 18. Vent vapor | 20000 B/D | overhead | product |
| 19. Reflux | 15000 B/D | 76° F. | 405 PSIA |
| 20. Heating coils | 56MM BTU/Hr | | |
| 21. Heavies separated from DeC$_2$ | 62000 B/D | 241° F. | 439 PSIA |
| 22. Combined bottoms product from stabilizer and de-ethanizer | 80000 B/D | 246° F. | 434 PSIA | note:
B/D = barrels/day

It is to be noted that the refrigeration system employed by the condenser uses 19.97MM BTU/Hr. If the stabilizer and the heat exchange steps of the present invention were not employed, the refrigeration system for a conventional de-ethanizer with similar operating conditions would use 21.7MM BTU/Hr. The process of the present invention, therefore, results in about a 1.73MM BTU/Hr savings in refrigeration.

Although the present invention has been described in conjunction with specific embodiments thereof, it is evident that many alternatives, modifications, variations, and equivalents, will be apparent to those skilled in the art in light of the foregoing disclosure of the invention. Accordingly, it is expressly intended that all such alternatives, modifications, variations, and equivalents which fall within the spirit and scope of the invention as defined in the appended claims be embraced thereby.

We claim:

1. A method for the removal of ethane from a feedstream comprising methane, ethane and higher components which comprises:
    (a) dividing the feedstream into two streams,
    (b) passing one stream to a stabilizer zone to thereby remove the heavier components as bottom and passing the second stream to a de-ethanizer,
    (c) feeding overhead vapor as obtained from the stabilizer to the de-ethanizer and introducing said vapors to the de-ethanizer in a location above the location said second stream is introduced,
    (d) combining the bottoms of the de-ethanizer with the bottoms of the stabilizer at a location outside the de-ethanizer and outside the stabilizer and removing said combined bottoms as de-ethanized product.

2. A method of claim 1 wherein the overhead vapors obtained from the stabilizer are cooled prior to introduction into the de-ethanizer.

3. A method of claim 2 wherein said stream passed to the stabilizer zone is cooled during said passage.

4. A method of claim 3 wherein said stream passed to the stabilizer is introduced into the upper section of the stabilizer, said second stream is introduced into the mid-section of said de-ethanizer, and said overhead vapors obtained from the stabilizer are introduced into the upper section of said de-ethanizer.

5. The method of claim 1 wherein said feedstream is natural gas liquids.

6. An apparatus useful in the removal of ethane from natural gas liquids stream comprising:
    a de-ethanizing means,
    a first conduit means for passing natural gas liquids to said de-ethanizing means,
    a stabilizing means for removing the heavy components of the natural gas liquids stream passed to the stabilizer thereby increasing the capacity of said de-ethanizing means,
    a second conduit means for passing natural gas liquids from said first conduit means to said stabilizing means,
    a third conduit means for passing overhead vapor from said stabilizing means to said de-ethanizing means,
    a fourth conduit means outside the de-ethanizer and the stabilizer for passing de-ethanized product out of the apparatus.

7. The apparatus of claim 6 wherein said third conduit means passes through a heat exchange means for cooling said overhead vapor being passed from the stabilizing means to the de-ethanizing means.

8. The apparatus of claim 7 wherein said second conduit means passes through a heat exchange means for cooling said natural gas passed from the first conduit means to the stabilizing means.

9. The apparatus of claim 8 wherein said second conduit means is connected to an introduction means in the upper portion of the stabilizing means,
    said first conduit means is connected to an introduction means in the mid-section of the de-ethanizing means, and
    said third conduit means is connected to an introduction means located in the upper section of the de-ethanizing means.

* * * * *